United States Patent [19]

Ghebre-Sellassie et al.

[11] Patent Number: 4,971,804
[45] Date of Patent: Nov. 20, 1990

[54] WATER DISPERSIBLE GEMFIBROZIL COMPOSITIONS

[75] Inventors: Isaac Ghebre-Sellassie, Stanhope; Robert H. Gordon, Dover; Uma Iyer, Mendham; Mahdi B. Fawzi, Road Flanders, all of N.J.

[73] Assignee: Warner-Lambert Company, Ann Arbor, Mich.

[21] Appl. No.: 305,081

[22] Filed: Feb. 2, 1989

[51] Int. Cl.$^5$ ................................................ A61K 9/16
[52] U.S. Cl. .................................... 424/490; 424/494; 424/497; 424/498
[58] Field of Search ............... 424/490, 498, 494, 496, 424/497

[56] References Cited

U.S. PATENT DOCUMENTS

| 4,132,753 | 1/1979 | Blichare et al. | 264/25 |
| 4,195,084 | 3/1980 | Ong | 424/238 |
| 4,263,272 | 4/1981 | Frigerio | 424/19 |
| 4,291,016 | 9/1981 | Nougaret | 424/35 |
| 4,533,562 | 8/1985 | Ikegami et al. | 427/3 |
| 4,661,162 | 4/1987 | Kurihara et al. | 106/169 |
| 4,797,288 | 1/1989 | Sharma | 424/498 X |

FOREIGN PATENT DOCUMENTS 2554717 5/1985 France .
2179254 3/1987 United Kingdom .

*Primary Examiner*—Thurman K. Page
*Attorney, Agent, or Firm*—Mathews, Woodbridge & Collins

[57] ABSTRACT

A water-dispersible formulation of gemfibrozil comprising finely divided particles of pure gemfibrozil uniformly coated with a mixture of a wax and at least one hydrophilic material, the coated particles in turn being overcoated with a minor amount of a surfactant.

4 Claims, No Drawings

WATER DISPERSIBLE GEMFIBROZIL COMPOSITIONS

The present invention relates to a water-dispersible formulation of gemfibrozil.

Background

Gemfibrozil, or 5-(2,5-dimethylphenoxy)-2,2-dimethylpentanoic acid, is a widely used antihyperlipoproteinemic agent which, because of the required large dose, generally is administered several times a day in the form of multiple capsules. Although it would be desirable to administer the agent in a water-dispersible formulation, this approach heretofore has been unattainable because of the unpleasant burning after-taste which it produces in the buccal mucosa.

It also would be beneficial to provide such water-dispersible formulations with sustained release properties so as to reduce the number of times the drug must be administered.

British Application No. 2,179,254 discloses compositions of analgesic propionic acid derivatives (such as ibuprofen) coated with a methacrylic-acrylic acid copolymer, then with a methacrylic ester copolymer, and finally with a mixture of polysorbate 80 and hydroxypropyl methylcellulose.

EPO-A No. 8600802 discloses sustained release compositions of polyethylene glycol and an amphiphilic compound.

French Application No. 2,554,717 discloses sustained release compositions which employs as the matrix a vinylpyrrolidone-vinyl acetate copolymer and an acrylic polymer cross-linked with polyallyl sucrose. (See also Belgian application No. 901007.)

U.S. Pat. No. 4,132,753 discloses controlled release granules in which the powdered medicament is heated so as to sink into a finely divided wax material.

U.S. Pat. No. 4,195,084 discloses a liquid suspension of finely ground tall oil sitosterols for use in reducing hypercholesteraemia.

U.S. Pat. No. 4,263,272 discloses three component formulations of bile acids which release gradually or in two stages.

U.S. Pat. No. 4,291,016 discloses pharmaceutical compositions having a matrix core coated with hydroxypropyl methyl cellulose.

U.S. Pat. No. 4,533,562 discloses tablets coated with a film-forming polymer such as hydroxypropyl methylcellulose and a liquid plasticizer such as polyethylene glycol.

U.S. Pat. No. 4,661,162 discloses an enteric soluble composition containing a mixture of an entericsoluble polymer such as (m)ethyl acrylate/methacrylate copolymers and a polyanionic polymer such as alginic acid and its salts.

Detailed Description

The present invention provides a water-dispersible formulation of gemfibrozil which can provide either immediate release, sustained release, or a combination of immediate and sustained release. In particular, this invention employs a formulation in which finely divided particles of pure gemfibrozil are uniformly coated with a mixture of a wax and at least one hydrophilic material and the coated particles in turn are overcoated with a minor amount of a surfactant, optionally together with flavoring agents.

The wax component is a conventional pharmaceutically acceptable microcrystalline wax. The hydrophilic materials are generally pharmaceutically acceptable compounds of the alcohol and ester type such as fatty acid alcohols, fatty acid esters, polyols, cellulose derivatives, and vinyl derivatives. A preferred hydrophilic material is stearyl alcohol.

The ratio of wax to hydrophilic material is from about 1:0.1 to about 0.1:1. A preferred range is from about 1:1 to about 5:1 of hydrophilic material:wax.

A coating formulation is prepared by mixing the wax and the hydrophilic material, optionally in the presence of a small amount of a plasticizer such as polyethylene glycol. Finely divided particles of pure gemfibrozil then are uniformly coated with this mixture.

The apparatus employed to treat substrates with the instant coating materials is not critical. Generally, any device will suffice as long as it can effectively coat the medicament or other ingestible agent with a sufficient quantity of the coating to hide the bad taste of the gemfibrozil. One preferred type of coating device is a fluid bed apparatus.

Following coating, the coated particles are in turn overcoated with a small amount of a pharmaceutically acceptable surfactant, as for example sodium lauryl sulfate or polysorbate 80 dissolved in a aqueous carrier. This surfactant overcoat can be admixed with suitable flavoring agents which provide a pleasant taste but do not affect the operation of the formulation. The overcoat formulation can be simply sprayed on the coated particles and the excess water then removed.

The resulting formulation has the appearance of a powder and is palatable and readily dispersible in ordinary water for oral administration. The coating composition has solubility characteristics which make it practically insoluble in the mouth, but readily disintegrates in the acid environment provided by the gastric juices of the stomach.

In a further embodiment, the formulation includes a first portion of finely divided particles of pure gemfibrozil uniformly coated with a mixture of a wax and hydrophilic material such as stearyl alcohol (to provide relatively immediate release as described above) and a second portion of the finely divided particles of pure gemfibrozil uniformly coated with a mixture of a wax and a hydrophobic material to provide relatively sustained release. A preferred hydrophobic material is hydrogenated castor oil.

The following examples will serve to further typify the nature of the invention but should not be construed as being a limitation on the scope thereof, which scope is defined solely by the appended claims.

EXAMPLE 1

A coating formulation is prepared from the following components:

| Ingredient | Parts by weight |
| --- | --- |
| Stearyl alcohol | 3 parts |
| Microcrystalline wax | 1 part |
| Polyethylene glycol 400 | 0.16 part |

Finely divided gemfibrozil particles are uniformly coated with the above formulation and then sprayed with an overcoat formulation of the following composition:

| | |
|---|---|
| Sodium lauryl sulfate | 3 parts |
| Purified water | 97 parts |

The overcoated particles are dried and packaged.

EXAMPLE 2

A sustained release coating formulation is prepared from the following components:

| Ingredient | Parts by weight |
|---|---|
| Hydrogenated castor oil | 3 parts |
| Microcrystalline wax | 1 part |
| Polyethylene glycol 400 | 0.08 part |

Finely divided gemfibrozil particles are uniformly coated with the above formulation and then sprayed with an overcoat formulation of the following composition:

| | |
|---|---|
| Sodium lauryl sulfate | 3 parts |
| Purified water | 97 parts |

The overcoated particles are dried and then mixed with an equal amount by weight of coated particles prepared in accordance with Example 1.

What is claimed is:

1. A water-dispersible formulation of gemfibrozil comprising finely divided particles of pure gemfibrozil uniformly coated with a mixture of a wax and at least one hydrophilic material selected from the group consisting of fatty acid alcohols, fatty acid esters, polyols, cellulose derivatives, and vinyl derivatives, the ratio of wax to hydrophilic material being from about 1:0.1 to about 0.1:1, said coated particles in trun being overcoated with an amount of a surfactant sufficient to improve the dispersibility of the formulation in water.

2. A water-dispersible formulation of gemfibrozil according to claim 1 wherein a first portion of the finely divided particles of pure gemfibrozil uniformly coated with a mixture of a wax and stearyl alcohol to provide relatively immediate release and a second portion of the finely divided particles of pure gemfibrozil uniformly coated with a mixture of a wax and hydrogenated castor oil to provide relatively sustained release.

3. A water-dispersible formulation of gemfibrozil according to claim 1 wherein the hydrophilic material is stearyl alcohol.

4. A water-dispersible formulation of gemfibrozil according to claim 1 wherein the surfactant is sodium lauryl sulfate.

* * * * *